Oct. 25, 1938. M. H. HORVATH Plant Pat. 298
ROSE
Filed Sept. 1, 1937
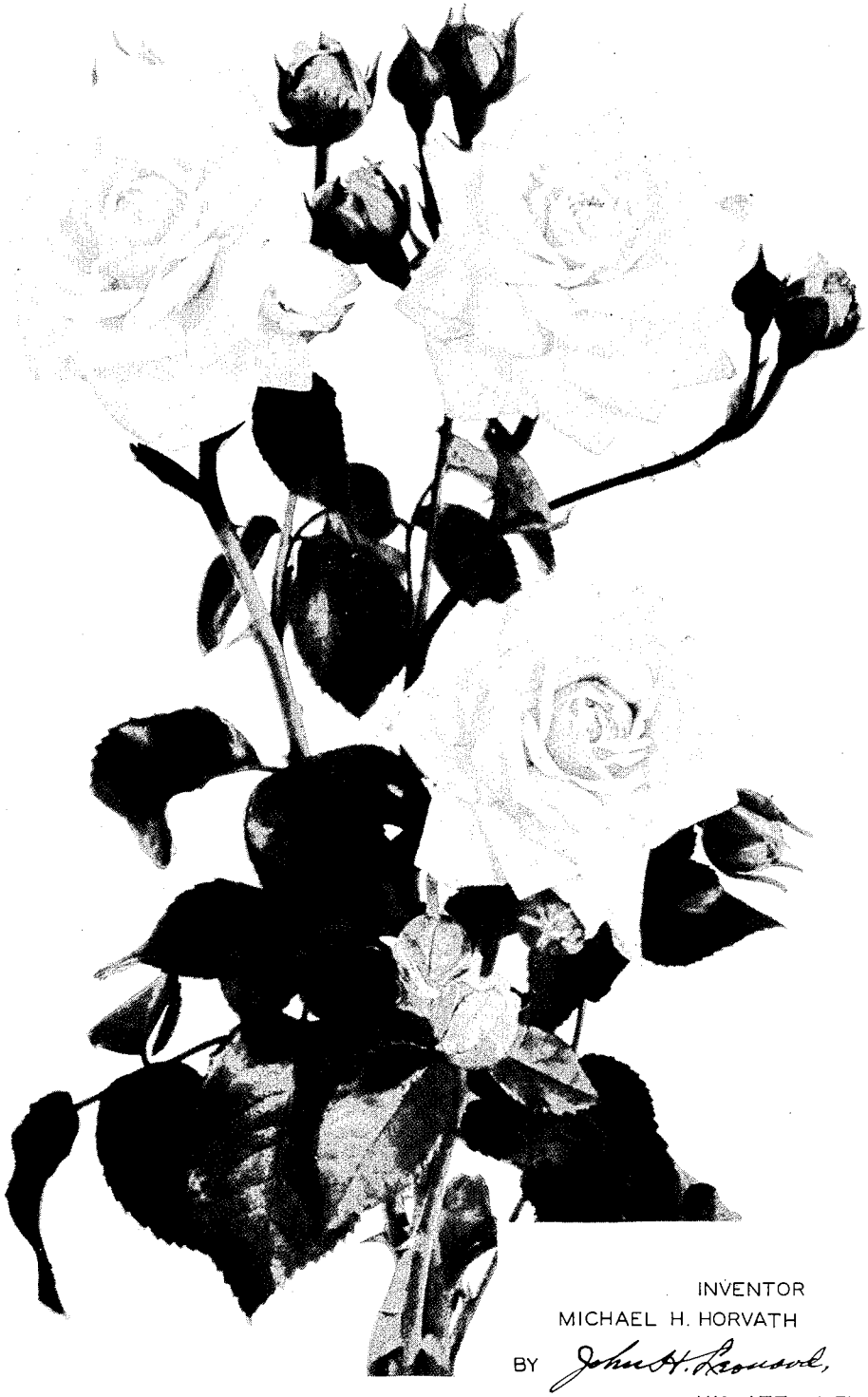
INVENTOR
MICHAEL H. HORVATH
BY John H. Leonard,
HIS ATTORNEY Patented Oct. 25, 1938

Plant Pat. 298

UNITED STATES PATENT OFFICE

298

ROSE

Michael H. Horvath, Mentor, Ohio

Application September 1, 1937, Serial No. 162,065

1 Claim. (Cl. 47—61)

This invention relates to a new variety of rose, a "Rosa Setigera Hybrid," produced by crossing the variety "Mrs. F. F. Prentiss", as the female parent, with the variety "Lady Alice Stanley" as the male parent. Successful asexual reproduction has been made.

The variety is of a hardy nature, it being a setigera hybrid, and it thrives without protection in the temperate region, and it can be successfully grown with protection in the colder regions where the growing of roses has been impossible or exceedingly difficult.

The foliage is of a shiny bright dark green color, comparable to "Deep Brunswick Green" of Maerz and Paul, Plate No. 24 A–12, and it is characteristically resistant to the ordinary rose maladies, such as mildew and blackspot.

The shrub reaches an ultimate height of from three to three-and-one-half feet, with a conspicuous upright and rounding growth and a spread of two to three feet, and with a very free growth of foliage from the top to the base of the shrub, all of which shrub characteristics make it very suitable and handsome for hedge purposes.

The compact flowers are imbricated in camellia-like form and they are borne singly and in clusters on stems fifteen to twenty-four inches long. The flowers are of a two-toned fresh pink color, corresponding to "Peach Blossom" Plate No. 1 C–2 and Plate No. 1 D–4, resembling miniature blooms of the variety "Lady Alice Stanley", and they grow abundantly on each plant. Eighty or more petals make up each flower, and they are so arranged as to make a full flower to the center, providing a rose flower which is distinctly rich in beauty.

The leaflets have veins which are of a reddish color, comparable to "Mayflower" Plate No. 3 J–3, and the prickles have a similar hue or cast, which blend well with the flower color.

The following is a detailed description of my new variety:

Parentage:
- *Seedlings.*—Seed parent—Setigera hybrid—Mrs. F. F. Prentiss. Pollen parent—Lady Alice Stanley.

Classification:
- *Botanic and commercial.*—Setigera hybrid.

*Flower*

Blooming habit:
- Location where observations were made—trial field of Michael H. Horvath, at Mentor, Ohio.
- Recurrent—perpetual blooming.

Bud:
- *Size.*—Medium—semi-polyantha like or larger.
- *Form.*—Globular—not affected by weather conditions.
- *Color.*—When sepals first divide—deep pink. When petals begin to unfurl—lighter pink. When half blown—two-toned pink.
- *Sepals.*—Smooth.
- *Calyx.*—Shape—rounded. Size—medium—semi-polyantha like. Aspect—smooth. Odor when rubbed—briar like.
- *Peduncle.*—Length—medium. Aspect—smooth. Color—light green. Strength—somewhat limber.
- *Opening.*—Opens well, not influenced by weather conditions.

Bloom:
- *Size.*—Semi-polyantha like—medium size.
- *Borne.*—In clusters or bracts.
- *Stems.*—Somewhat limber.
- *Form.*—When first open—semi-globular. Permanence—retains form well.
- *Petalage.*—Number of petals under normal conditions—80 or more.
- *Color.*—Center of flower—deep pink. Outer petals—lighter pink. Base of petals—light pink. Inside of petals—two-toned pink. Reverse of petals—dark pink. General tonality from a distance—two-toned fresh pink color.
- *Variegations.*—None.
- *Discoloration.*—General tonality at end of first and second days—no fading. Third day—no fading.

Petals:
- *Texture.*—Medium.
- *Appearance.*—Inside—light pink. Outside—darp pink.
- *Form.*—Semi-globular.
- *Arrangement.*—Imbricated.
- *Petaloids in center.*—Many.
- *Persistence.*—Drop cleanly.
- *Fragrance.*—Slight briar scent.
- *Nature.*—Briar scent.
- *Lasting quality.*—On the plant and as cut flower—good on plant or cut.

Genital organs:
- *Stamens.*—Sparse, sterile.
- *Color.*—White.
- *Arrangement.*—Irregular.
- *Stamens, filaments (threads).*—Short.
- *Color.*—White.
- *Pollen.*—Yellow.
- *Styles.*—Irregular.
- *Stigmas.*—White.
- *Ovaries.*—None.

Fruit:
*Variety.*—Is generally sterile.
*Sepals.*—Fall after flowering.

*Plant*

Form: Bush.
Growth: Two to four feet.
Foliage: Glabrous.
*Size.*—Medium.
*Quantity.*—Ample.
*Color.*—New foliage—upper side—glabrous green. Under side—reddish green. Old foliage—shiny bright dark green.
*Shape.*—Irregular, some oval pointed, some rounded tips.
*Texture.*—Upper side—glabrous and shiny. Under side—smooth. Ribs and veins—prominent.
*Edge.*—Serrated.
*Serration.*—Regular.
*Rachis.*—Prickly. Color—reddish green. Under side—same with prickles.
*Stipules.*—Smooth.
Disease resistance: Resistant.
Wood:
*New wood.*—Color—reddish green. Bark—green.
*Old wood.*—Color—olive green. Bark—smooth dark green.

Thorns (Thorns are divided into thorns, prickles and short needles):
*Quantity.*—On main stalks from base—irregular, large, downward, hooked. On laterals from stalk—same as above.
*Form.*—Wide base.
*Color when young.*—Red.
*Position.*—Irregular.
*Prickles.*—Few irregularly distributed.
*Short needles.*—None.

The drawing illustrates many of the characteristics which are not found in the parent stock and which make the variety of more value as a plant and increase its beauty.

Having now fully shown and described my new rose, and the mode of its production, what I claim and desire to secure by Letters Patent of the United States, is:

A rose as herein shown and described and distinguished by its hardy character, shrub growth very suitable for hedge purposes, shiny bright dark green foliage resistant to rose maladies and having veins prominent with a reddish hue or cast, distinctive full flowers imbricated in camellia-like form and of a two-toned pink color resembling miniature Lady Alice Stanley blooms profusely borne singly and in clusters and in a manner making them very suitable as cut flowers.

MICHAEL H. HORVATH.